United States Patent [19]

Meguro et al.

[11] Patent Number: 4,603,135

[45] Date of Patent: Jul. 29, 1986

[54] SUBSTITUTED PIPERAZINYL ALKYL ESTERS OF 2-AMINO-4-ARYL-1,4-DIHYDRO-6-ALKYL-3,5-PYRIDINEDICARBOXYLATES

[75] Inventors: Kanji Meguro, Hyogo; Akinobu Nagaoka, Kawanishi, both of Japan

[73] Assignee: Takeda Chemical Industries, Ltd., Doshomachi, Japan

[21] Appl. No.: 654,247

[22] Filed: Sep. 25, 1984

[30] Foreign Application Priority Data

Oct. 17, 1983 [JP] Japan .................. 58-194691
Oct. 31, 1983 [JP] Japan .................. 58-205579

[51] Int. Cl.⁴ .............. C07D 401/12; A61K 31/495
[52] U.S. Cl. .............. 514/252; 544/360; 546/321
[58] Field of Search .......... 544/360; 424/250; 546/321; 514/252

[56] References Cited

U.S. PATENT DOCUMENTS

| | | | |
|---|---|---|---|
| 3,472,853 | 10/1969 | Archer | 544/394 |
| 3,485,847 | 12/1969 | Bossert et al. | 546/321 |
| 3,905,970 | 9/1975 | Bossert et al. | 424/250 |
| 3,959,292 | 5/1976 | Meyer et al. | 544/365 |
| 3,974,275 | 8/1976 | Bossert et al. | 544/360 |
| 3,985,758 | 10/1976 | Murakami et al. | 546/321 |
| 3,996,234 | 12/1976 | Bossert et al. | 544/360 |
| 4,031,104 | 6/1977 | Bossert et al. | 544/360 |
| 4,038,399 | 7/1977 | Bossert et al. | 544/360 |
| 4,430,333 | 2/1984 | Campbell et al. | 546/321 |

FOREIGN PATENT DOCUMENTS 1029022 8/1977 Canada ................ 546/321
1369401 10/1974 United Kingdom ........ 546/257

Primary Examiner—George F. Lesmes
Assistant Examiner—S. A. Gibson
Attorney, Agent, or Firm—Wegner & Bretschneider

[57] ABSTRACT

Dihydropyridine derivatives and acid addition salts thereof which are of use as prophylactic or/and therapeutic drugs for cardiovascular diseases, said dihydropyridine derivatives having the formula

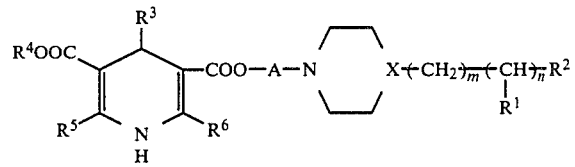

wherein
$R^1$ is a hydrogen atom or an aryl,
$R^2$ and $R^3$ are the same or different and each is an aryl,
$R^4$ and $R^6$ are the same or different and each is a lower alkyl,
$R^5$ is amino or a lower alkyl,
A is an alkylene,
X is N or CH and
m and n are the same or different
and each is 0 or 1,
with the proviso that when X is N, $R^5$ is amino.

11 Claims, No Drawings

SUBSTITUTED PIPERAZINYL ALKYL ESTERS OF 2-AMINO-4-ARYL-1,4-DIHYDRO-6-ALKYL-3,5-PYRIDINEDICARBOXYLATES

It is known that several dihydropyridines having a skeletal structure similar to that of compounds of this invention have coronary artery dilating and antihypertensive activities.

However, a broad field of synthetic chemistry remains yet to be explored for dihydropyridine derivatives and it is true, even the more, of pharmacologic investigations of such compounds.

This invention relates to novel dihydropyridine derivatives having desirable pharmacological activities.

More particularly, this invention provides dihydropyridine derivatives of the formula $$R^4OOC\underset{R^5}{\underset{|}{\diagdown}}\underset{N}{\overset{R^3}{\diagup}}\underset{H}{\overset{|}{\diagdown}}\underset{R^6}{\diagup}-COO-A-N\diagup\diagdown X-(CH_2)_m-(CH)_n-R^2 \atop |R^1 \qquad (I)$$

wherein
R$^1$ is a hydrogen atom or an aryl,
R$^2$ and R$^3$ are the same or different and each is an aryl,
R$^4$ and R$^6$ are the same or different and each is a lower alkyl,
R$^5$ is amino or a lower alkyl,
A is an alkylene,
X is N or CH and
m and n are the same or different and each is 0 or 1, with the proviso that when X is N, R$^5$ is amino, or a pharmaceutically acceptable salt thereof, which have potent and long-lasting antihypertensive, peripheral vasodilating, coronary vasodilating, cerebral vasodilating and other activities and are useful as, for instance, drugs.

Referring to the above formula (I), the aryl groups respectively represented by R$^1$, R$^2$ and R$^3$ may be the same or different and each is, for example, a phenyl group. This phenyl group may have one or more substituents each optionally selected from among halogen, nitro, trifluoromethyl, lower alkyl, lower alkoxy and so forth. The position of each substituent on the benzene ring is optional. For R$^3$, the ortho and/or meta position is a particularly preferred position for such substituent(s).

The halogen as the above-mentioned substituent includes fluorine, chlorine, bromine and iodine, and fluorine and chlorine are particularly preferred. The lower alkyl as the substituent preferably contains 1 to 6 carbon atoms and may be either straight or branched, including, among others, methyl, ethyl, propyl, isopropyl, butyl, isobutyl, sec-butyl, t-butyl, pentyl, isopentyl, neopentyl and hexyl. Those alkyls containing 1 to 4 carbon atoms are particularly preferred.

The lower alkoxy substituent preferably contains 1 to 3 carbon atoms. Examples are methoxy, ethoxy, propoxy and isopropoxy.

The lower alkyl groups respectively represented by R$^4$, R$^5$ and R$^6$ include the above-mentioned ones containing 1 to 6 carbon atoms, preferably 1 to 4 carbon atoms.

The alkylene group represented by A preferably contains 2 to 4 carbon atoms and may be either straight or branched. Examples are ethylene, trimethylene, propylene, tetramethylene and 1,2-dimethylethylene.

When X is N, the ring containing X occurs as a piperazine ring, whereas, when X is CH, said ring occurs as a piperidine ring.

In case where m is 0 and n is 0, R$^2$ is in direct connection with the piperazine or piperidine ring.

The compounds of the invention, namely the compounds of the formula (I), can be produced by subjecting any one of the fragments capable of constituting a dihydropyridine derivative of the formula (I) to cyclo-dehydration reaction with the remaining fragment(s) capable of constituting said derivative (I).

$$R^4OOC\underset{R^5}{\underset{|}{\diagdown}}\underset{N}{\overset{R^3}{\diagup}}\underset{H}{\overset{|}{\diagdown}}\underset{R^6}{\diagup}-COO-A-N\diagup\diagdown X-(CH_2)_m-(CH)_n-R^2 \atop |R^1 \qquad (I)$$

More specifically, the compounds of the invention represented by the formula (I), wherein R$^5$ is a lower alkyl and X is CH, are produced, for example, by one of the following processes:

Process A $$\underset{H_2N}{\overset{R^{5'}}{\diagdown}}C=CHCOOR^4 + R^3-CHO + \qquad (II) \qquad (III)$$

$$\underset{\underset{\underset{O}{\diagdown}}{C}}{\overset{CH_2}{\underset{|}{|}}}COO-A-N\diagup\diagdown-(CH_2)_m-(CH)_n-R^2 \atop |R^1 \longrightarrow$$
$$R^6 \qquad (IV)$$

$$R^4OOC\underset{R^{5'}}{\underset{|}{\diagdown}}\underset{N}{\overset{R^3}{\diagup}}\underset{H}{\overset{|}{\diagdown}}\underset{R^6}{\diagup}-COO-A-N\diagup\diagdown-(CH_2)_m-(CH)_n-R^2 \atop |R^1 \qquad (I')$$

Process B $$\underset{R^{5'}}{\overset{COOR^4}{\underset{|}{\overset{|}{\underset{\underset{O}{\diagup}}{C}}}}}\overset{CH_2}{\underset{|}{|}} + (III) +$$
$$(V)$$

$$\underset{H_2N}{\overset{R^6}{\diagdown}}C=CHCOO-A-N\diagup\diagdown-(CH_2)_m-(CH)_n-R^2 \atop |R_1 \longrightarrow$$
$$(VI)$$

-continued

Process C

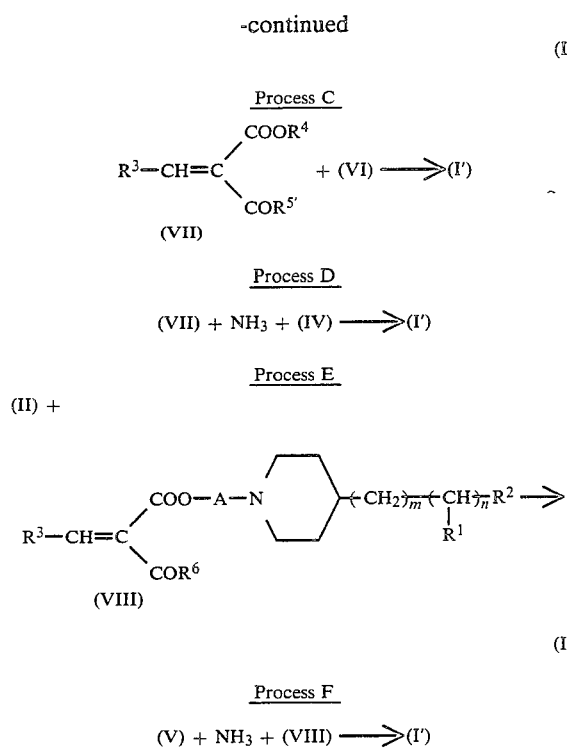

Process D (VII) + NH₃ + (IV) ⟶ (I')

Process E

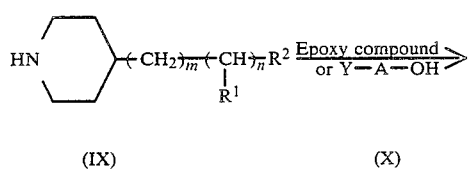

(II) +

R³—CH=C(COO—A—N⟨...⟩(CH₂)ₘ(CH)ₙR² / COR⁶)
(VIII)

⟶ (I')

Process F (V) + NH₃ + (VIII) ⟶ (I')

In the above formulas, $R^{5'}$ is a lower alkyl.

In the following, the above processes are described in more detail.

PROCESS A

In this process, compounds (II), (III) and (IV) are reacted in an appropriate solvent to give (I'). This reaction is generally carried out at above 20° C. to about 160° C., preferably at about 50° C. to about 130° C., most conveniently at the boiling point of the solvent used. As such solvent, there may be used any of those solvents which are inert to the reaction, such as alkanols (e.g. methanol, ethanol, propanol, isopropanol, butanol, secbutanol) ethers (e.g. ethyl ether, dioxane, tetrahydrofuran, ethylene glycol monomethyl ether, ethylene glycol dimethyl ether), acetic acid, pyridine, N,N-dimethylformamide, dimethyl sulfoxide and acetonitrile. It generally takes 0.5-15 hours for the reaction to be complete. (II), (III) and (IV) are used in a molar ratio such that two of the three reactants are each used in an amount of 1-1.5 moles per mole of the remaining one. The starting compound (II) is known or, if unknown, can be produced by the known method [cf., for example, J. Am. Chem. Soc., 67, 1017 (1945)]. The compound (IV) can be produced, for example, in the following manner:

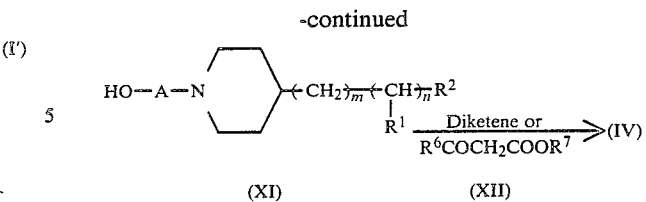

In the above formulas, $R^7$ is a lower alkyl group, Y is a halogen atom and the other symbols are as defined above.

First, (XI) is synthesized by reacting (IX) with an epoxy compound containing an alkylene group corresponding to the moiety A (e.g. ethylene oxide, propylene oxide) or a halohydrin of formula (X). The reaction of (IX) with the epoxy compound is generally conducted in an appropriate solvent (e.g. water, methanol, ethanol, dioxane, tetrahydrofuran) at 20° C. to 100° C. In synthesizing (XI) by reacting (IX) with (X), the reaction is preferably carried out in the presence of a base, such as sodium carbonate or potassium carbonate, in an appropriate solvent selected from the group consisting of those mentioned above and further acetone, methyl ethyl ketone, N,N-dimethylformamide and so on, at 20° C. to 100° C. In formula (X), the halogen atom represented by Y is chlorine, bromine or iodine. When Y is a chlorine or bromine atom, the presence of about 0.1 to about 1 mole of sodium iodide, potassium iodide or the like per mole of (IX) may promote the reaction.

Then, (IV) is synthesized by reacting (XI) with diketene or a β-keto ester of formula (XII). The reaction between (XI) and diketene is generally effected by heating a mixture of these at about 40° C. to about 130° C. In that case, an appropriate solvent inert to the reaction may be added. This reaction gives a compound (IV) in which R⁶ is methyl. Alternatively, (IV) can also be produced by reacting (XI) with a β-keto ester (XII), and this reaction can be conducted in the presence of a base, such as sodium methoxide, sodium ethoxide, potassium t-butoxide, sodium hydride, sodium amide or metallic sodium, in an appropriate inert solvent or without using any solvent, at about 20° C. to about 100° C.

PROCESS B

This process can be carried out under substantially the same conditions as process A. The starting compound (VI) for this process can be synthesized by reacting the starting compound (IV) for process A with ammonia. Thus, (IV) is dissolved in an appropriate solvent (e.g. methanol, ethanol, ethyl ether, dioxane, tetrahydrofuran), and an excessive amount of gaseous ammonia is passed through the solution at about 0° C. to about 60° C., or a solution of ammonia in a solvent such as mentioned above is added to the above solution and the mixture is kept at about 0° C. to about 60° C. in a tightly closed vessel, whereby, in either case, (VI) can easily be synthesized.

PROCESS C

In this process, an arylmethylene-β-keto ester (VII) is reacted with compound (VI) to give the desired compound (I'). This reaction is carried out under substantially the same conditions as process A, using 0.3-1.5 moles of (VI) per mole of compound (VII). The starting arylmethylene-β-keto ester (VII) is either known or, if unknown, producible from an aldehyde (III) and a β- keto ester (V) by the known method [cf., for example, Organic Reactions, 15, 204–599 (1967)].

PROCESS D

In this process, ammonia and compound (IV) are simultaneously used in place of (VI) in process C. In this case, it is considered that ammonia first reacts with (IV) to give (VI) and (VI) then reacts with (VII). In fact, this reaction can be conducted under substantially the same conditions as process C. (IV) is used generally in an amount of 0.8 to 1.5 moles and ammonia in an amount of 1 to 5 moles per mole of (VII).

PROCESS E

This process can be carried out by reacting (II) with (VIII) under substantially the same conditions as process C. The starting arylmethylene-β-keto ester (VIII), like (VII), can be synthesized by reacting an aldehyde (III) with a β-keto ester (IV) by the known method [cf., for example, Organic Reactions, 15, 204–599 (1967)]. For the reaction in this process, (II) is generally used in an amount of 0.8–1.5 moles per mole of (VIII).

PROCESS F

In this process, ammonia and (V) are used in place of (II) in process E. In this case, it is considered that ammonia first reacts with (V) to give (II) and then (II) reacts with (VIII). In fact, this reaction can be conducted under substantially the same conditions as Process E. (V) is generally used in an amount of 0.8–1.5 moles and ammonia in an amount of 1–5 moles per mole of (VIII).

The compounds of the invention represented by the formula (I), wherein $R^5$ is amino, can be produced easily by the following process.

Process G

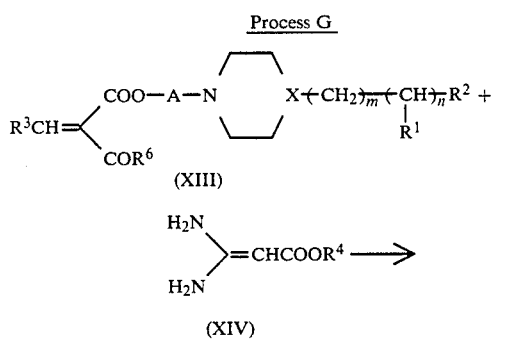

(XIII)

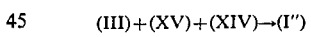

(XIV)

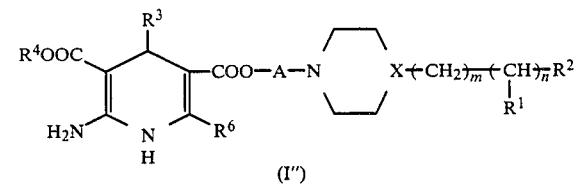

(I″)

This reaction is carried out by contacting compound (XIII) with compound (XIV) in an organic solvent. Any solvent inert to the reaction may be used as the solvent. Suitable examples are alcohols, such as methanol, ethanol, propanol, 2-propanol and butanol, and ethers, such as dioxane, tetrahydrofuran, dimethoxyethane and diethyl ether, and further acetonitrile, pyridine, dimethylformamide, dimethyl sulfoxide and the like. The reaction temperature is generally selected within the range of 20°–200° C. It is, however, preferable to carry out the reaction at the boiling point of the solvent employed. The amidinoacetic acid ester (XIV) may be used either in the free form or in the acid addition salt form. When an acid addition salt is used, the reaction can be effected by adding a base (e.g. alkali metal alcoholate) to the reaction system. (XIV) may also be represented by the formula:

which indicates the tautomeric structure of (XIV). The present invention also covers the use of (XIV′). In carrying out the reaction between (XIII) and (XIV), these are used in equimolar amounts or one of them is used in a slight excess.

The arylmethylene-β-ketocarboxylic acid ester (XIII) to be used as the starting material can be produced from an aldehyde (III) and a β-ketocarboxylic acid ester (XV) by the conventional method [cf. for example, Organic Reactions, 15, 204–599 (1967)], as shown below.

$R^3$—CHO +

(III)

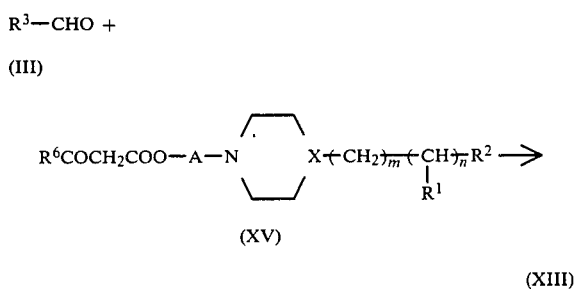

(XIII)

Therefore, in carrying out the Process G, (III) and (XV), instead of using (XIII), may simultaneously be reacted with (XIV) as shown below in some instances. In that case, (XIII) is formed in the reaction system and then reacts with (XIV) to give the desired compound (I″).

(III)+(XV)+(XIV)→(I″)

(XV) can be synthesized by the following process (1) or (2):

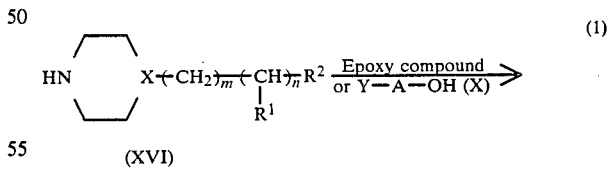

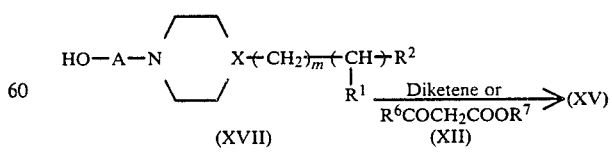

Reaction conditions of each step of this process are the same as those mentioned above in the synthesis of (IV). (2) Those compounds (XV) in which X is N and at least one of m and n is other than 0, namely (XV′), can be produced in the following manner:

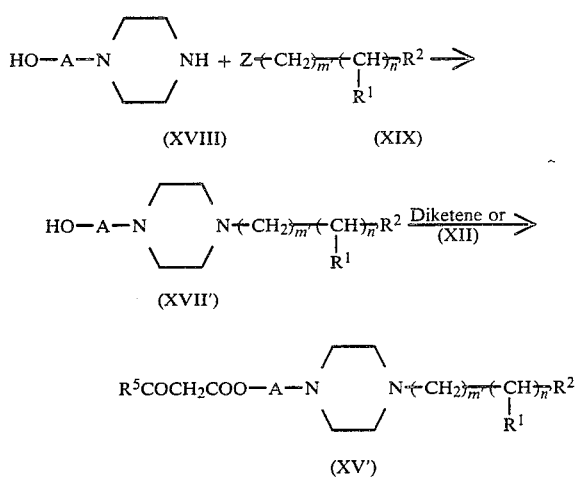

In the above formulas, Z is a leaving group and m' and n' each is an integer of 0 or 1 but at least one of m' and n' is other than 0.

The leaving group represented by Z includes, among others, halogen atoms such as mentioned above in relation to Y and sulfonyloxy groups such as methanesulfonyloxy, benzenesulfonyloxy and p-toluenesulfonyloxy. The reaction between (XVIII) and (XIX) and the reaction between (XVII') and diketene or (XII) can be conducted under the same conditions as the reaction between (XVI) and (X), and the reaction between (XVII) and diketene or (XII) in the abovementioned process (1), respectively.

The dihydropyridine derivatives (I) produced in the above manner are novel compounds and can be isolated in an optional purity by the per se known method of separation and purification, such as concentration, extraction, chromatography, reprecipitation, recrystallization, and so forth. Since the compounds (I) have a basic group, they can be converted to acid additon salts by a per se conventional method. Such salts include, among others, salts with inorganic acids (e.g. hydrochloride, hydrobromide, phosphate, sulfate) and salts with organic acids (e.g. acetate, oxalate, malonate, succinate, maleate, fumarate, malate, tartrate, methanesulfonate).

The compounds (I) and salts thereof provided by the present invention are of low toxicity, display potent and long-lasting antihypertensive, peripheral vasodilating, coronary vasodilating, cerebral vasodilating and other activities in mammals (e.g. mice, rats, rabbits, dogs, cats, humans) and are useful, for example, as drugs for the prevention and treatment of diseases of the circulatory system in humans, such as hypertension, ischemic heart diseases (angina pectoris, myocardial infarction, etc.) and cerebral and peripheral circulatory disturbances (cerebral infarction, transient ischemic attack, etc.). In particular, they are superior in activity intensity and duration to the prior art dihydropyridine derivatives (e.g. nifedipine, nicardipine) and, when used in the prevention or treatment of hypertension, for instance, they can produce stable hypotensive effects by a smaller number of administrations (e.g. once or twice a day).

In using as drugs such as mentioned above, the compounds (I) and salts thereof can be administered either orally or parenterally in the form of powders, granules, tablets, capsules, injections and so forth prepared by admixing them with appropriate pharmaceutically acceptable carriers, excipients and/or diluents. The dose depends on the route of administration, the symptom, the patient's body weight and/or age, and other factors. In administering orally to adult human hypertensive patients, for instance, they are desirably administered in a daily dose of 0.05–20 mg/kg body weight, preferably 0.1–4 mg/kg body weight, in one to several divided doses per day.

In the following, the results of a pharmacological test which demonstrate the efficacy of the compounds (I) of the present invention are given.

ANTIHYPERTENSIVE ACTIVITY

Male spontaneously hypertensive rats aged 10–11 weeks were used in groups of 3–6 animals. For blood pressure measurement, Ueda Medical's automatic blood pressure measuring apparatus (USM-105R) was used and the systolic pressure in the rat caudal artery was measured.

Each test compound was suspended in 5% gum arabic solution and administered orally in a dose of 10 mg/kg, and the blood pressure was measured 1, 5 and 8 hours after administration. The data obtained are given below in the table in terms of the average value (mmHg).

| Compound Example No. | Systolic blood pressure (mmHg) | | | |
|---|---|---|---|---|
| | Before administration | 1 hour later | 5 hours later | 8 hours later |
| 1 | 197 | 136 | 115 | 133 |
| 2 | 187 | 118 | 107 | 115 |
| 3 | 193 | 138 | 109 | 122 |
| 4 | 197 | 173 | 164 | 182 |
| 5 | 194 | 158 | 133 | 147 |
| 6 | 194 | 171 | 135 | 136 |
| 7 | 198 | 162 | 153 | 162 |
| 8 | 190 | 180 | 118 | 126 |
| 9 | 185 | 188 | 161 | 165 |
| 10 | 204 | 131 | 147 | 159 |
| 11 | 200 | 119 | 126 | 146 |
| 12 | 209 | 120 | 109 | 110 |
| 13 | 192 | 130 | 119 | 150 |
| 14 | 198 | 152 | 137 | 142 |
| 15 | 197 | 144 | 139 | 162 |
| Nifedipine[1] | 196 | 151 | 193 | 202 |
| Nicardipine.HCl[2] | 186 | 153 | 180 | 185 |

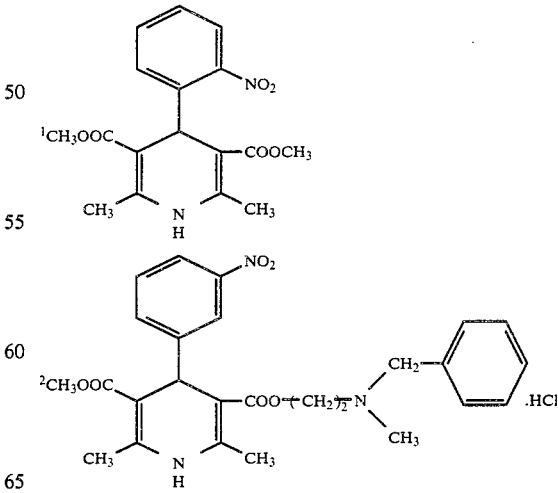

It will be apparent from the table that compounds of this invention show much more long-lasting hypotensive action as compared with the known dihydropyridine derivatives (nifedipine and nicardipine).

The following examples and reference examples illustrate the invention in more detail. In the examples, the melting point determination was always performed by the hot plate method and the values given are uncorrected ones.

EXAMPLE 1

(1) A mixture of m-nitrobenzaldehyde (1.67 g), 2-(4-benzhydryl-1-piperazinyl)ethyl acetoacetate (4.20 g), benzene (40 ml) and piperidine (0.05 g) was refluxed for 4 hours, during which time the water produced was removed using a Dean-Stark trap. The mixture was washed with water and dried (MgSO$_4$). The solvent was then distilled off and the residue was purified by column chromatography on silica gel (100 g) [eluent: ethyl ether-ethyl acetate (10:1, v/v)] to give 2-(4-benzhydryl-1-piperazinyl)ethyl 2-(3-nitrobenzylidene)acetoacetate as an oil. Yield 4.37 g.

NMR(CDCl$_3$)δ: 2.38(3H,s,COCH$_3$), 4.14–4.53(3H,m, —COO,uns/CH/ $_2$CH$_2$—, >N—CH<), 7.10–8.75(14H,m).

(2) Sodium (0.20 g) was dissolved in dry ethanol (10 ml) and the thus-obtained sodium ethylate solution was added dropwise to a solution of 2-(4-benzhydryl-1-piperazinyl)ethyl 2-(3-nitrobenzylidene)acetoacetate (4.37 g) and ethyl amidinoacetate hydrochloride (1.42 g) in dry ethanol (10 ml) with stirring under reflux over a period of about 15 minutes. The mixture was further refluxed for 5 minutes. The resulting NaCl was filtered off and the filtrate was concentrated under reduced pressure. The residue was purified by column chromatography on silica gel (120 g). From the eluate with ethyl ether-ethyl acetate (10:1, v/v), there was obtained 5-[2-(4-benzhydryl-1-piperazinyl)ethyl] 3-ethyl 2-amino-1,4-dihydro-6-methyl-4-(3-nitrophenyl)-3,5-pyridinedicarboxylate as a yellow powder. Yield 3.22 g. To a solution of 2.48 g of this product in ethanol was added a solution of oxalic acid in ethanol to give the oxalate as crystals. Yield 2.52 g. Recrystallization from ethanol-ethyl ether gave yellow crystals (1.83 g). m.p. 152°–153° C.

Elemental analysis: Calcd. for C$_{35}$H$_{39}$N$_5$O$_6$.C$_2$H$_2$O$_4$: C, 62.09; H, 5.77; N, 9.78; Found: C, 62.47; H, 6.09; N, 9.57.

In the same manner as Example 1 the following compounds were obtained.

EXAMPLE 2

5-[2-[4-(4,4'-Dimethylbenzhydryl)-1-piperazinyl]ethyl] 3-ethyl 2-amino-1,4-dihydro-6-methyl-4-(3-nitrophenyl)-3,5-pyridinedicarboxylate oxalate: m.p. 180°–182° C.

Elemental analysis Calcd. for C$_{37}$H$_{43}$N$_5$O$_6$.C$_2$H$_2$O$_4$.½H$_2$O: C, 62.22; H, 6.16; N, 9.30; Found: C, 62.43; H, 6.03; N, 9.18.

EXAMPLE 3

5-[2-[4-(4,4'-Difluorobenzhydryl)-1-piperazinyl]ethyl 3-isopropyl 2-amino-1,4-dihydro-6-methyl-4-(3-nitrophenyl)-3,5-pyridinedicarboxylate oxalate: m.p. 143°–144° C.

Elemental analysis Calcd. for C$_{36}$H$_{39}$F$_2$N$_5$O$_6$.C$_2$H$_2$O$_4$.½H$_2$O: C, 58.91; H, 5.46; N, 9.04; Found: C, 59.14; H, 5.32; N, 8.92.

EXAMPLE 4

5-[2-[4-(2,2-Diphenylethyl)-1-piperazinyl]ethyl] 3-ethyl 2-amino-1,4-dihydro-6-methyl-4-(3-nitrophenyl)-3,5-pyridinedicarboxylate oxalate: m.p.206°–208° C.

Elemental analysis: Calcd. for C$_{36}$H$_{41}$N$_5$O$_6$.C$_2$H$_2$O$_4$: C, 62.54; H, 5.94; N, 9.60; Found: C, 62.90; H, 5.91; N, 9.28.

EXAMPLE 5

5-[2-(4-Benzhydrylpiperidino)ethyl] 3-ethyl 2-amino-1,4-dihydro-6-methyl-4-(3-nitrophenyl)-3,5-pyridinedicarboxylate oxalate: m.p. 153°–155° C.

Elemental analysis: Calcd. for C$_{36}$H$_{40}$N$_4$O$_6$.C$_2$H$_2$O$_4$: C, 63.86; H, 5.92; N, 7.84; Found: C, 63.87; H, 5.89; N, 7.73.

EXAMPLE 6

5-[2-(4-Benzhydryl-1-piperazinyl)ethyl] 3-ethyl 2-amino-1,4-dihydro-6-methyl-4-(3-trifluoromethylphenyl)-3,5-pyridinedicarboxylate: pale yellow powder.
IR(Nujol)cm$^{-1}$: 3450, 3325, 1700, 1685, 1670.
NMR(CDCl$_3$)δ: 1.16(3H,t,J=7.2 Hz), 2.24(3H,s), 2.39(8H, broad), 2.52(2H,t,J=6.6 Hz), 3.87–4.23(5H,m), 4.89(1H, s), 6.14(2H,s,NH$_2$), 6.67(1H,s,NH), 7.08–7.53(14H,m).

Elemental analysis: Cacld. for C$_{36}$H$_{39}$F$_3$N$_4$O$_4$: C, 66.65; H, 6.06; N, 8.64; Found: C, 66.81; H, 6.16; N, 8.60.

EXAMPLE 7

5-[2-(4-Benzhydryl-1-piperazinyl)ethyl] 3-isopropyl 2-amino-1,4-dihydro-6-methyl-4-(3-trifluoromethylphenyl)-3,5-pyridinedicarboxylate: pale yellow powder.
IR(Nujol)cm$^{-1}$: 3440, 3315, 1700, 1670.
NMR(CDCl$_3$)δ: 1.00(3H,d,J=6 Hz), 1.20(3H,d,J=6 Hz), 2.22 (3H,s), 2.40(8H,broad), 2.52(2H,t,J=6 Hz), 4.10(2H,t, J=6 Hz), 4.17(1H,s), 4.87(1H,s), 4.88(1H,m), 6.17(2H, broad s,NH$_2$), 6.75(1H,s,NH), 7.0–7.55(14H,m).

Elemental analysis: Calcd. for C$_{37}$H$_{41}$F$_3$N$_4$O$_4$: C, 67.05; H, 6.24; N, 8.45; Found: C, 67.06; H, 6.27; N, 8.47.

EXAMPLE 8

5-[2-[4-(4,4'-Dichlorobenzhydryl)-1-piperazinyl]ethyl 3-ethyl 2-amino-1,4-dihydro-6-methyl-4-(3-nitrophenyl)-3,5-pyridinedicarboxylate dihydrochloride: m.p. 174°–175° C.

Elemental analysis: Calcd. for C$_{35}$H$_{37}$Cl$_2$N$_5$O$_6$.2HCl.H$_2$O: C, 53.51; H, 5.26; N, 8.92; Found: C, 53.58; H, 5.21; N, 8.85.

EXAMPLE 9

5-[2-[4-(4,4'-Dichlorobenzhydryl)-1-piperazinyl]ethyl 3-ethyl 2-amino-4-(2,3-dichlorophenyl)-1,4-dihydro-6-methyl-3,5-pyridinedicarboxylate trihydrochloride: m.p. 187°–188° C.

Elemental analysis: Calcd. for C$_{35}$H$_{36}$Cl$_4$N$_4$O$_4$.3HCl: C, 50.78; H, 4.75; N, 6.77; Found: C, 50.69; H, 4.78; N, 6.70.

EXAMPLE 10

5-[2-[4-(3-Chlorophenyl)1-piperazinyl]ethyl] 3-ethyl 2-amino-1,4-dihydro-6-methyl-4-(3-nitrophenyl)-3,5-pyridinedicarboxylate: yellow powder.
IR(Nujol)cm$^{-1}$: 3450, 3315, 1670.
NMR(CDCl$_3$)δ: 1.20(3H,t,J=6.9 Hz), 2.30(3H,s), 2.47–2.74 (6H,m), 2.99–3.23(4H,m), 4.06(2H,q,J=6.9

Hz), 4.18 (2H,t,J=6 Hz), 5.00(1H,s), 6.32(2H,broad s,NH$_2$), 6.65–8.18(8H,m), 6.97(1H,s,NH).

Elemental analysis: Calcd. for C$_{28}$H$_{32}$ClN$_5$O$_6$: C, 59.00; H, 5.66; N, 12.29; Found: C, 58.69; H, 5.30; N, 11.98.

EXAMPLE 11

3-Isopropyl 5-[2-[4-(2-methylphenyl)-1-piperazinyl]ethyl]2-amino-1,4-dihydro-6-methyl-4-(3-nitrophenyl)-3,5-pyridinedicarboxylate oxalate: m.p. 157°–160° C.

Elemental analysis: Calcd. for C$_{30}$H$_{37}$N$_5$O$_6$·C$_2$H$_2$O$_4$: C, 58.80; H, 6.01; N, 10.71; Found: C, 58.56; H, 6.00; N, 10.59.

EXAMPLE 12

3-Ethyl 5-[2-[4-(4,4'-difluorobenzhydryl)-1-piperazinyl]ethyl] 2-amino-1,4-dihydro-6-methyl-4-(3-nitrophenyl)-3,5-pyridinedicarboxylate: yellow powder, m.p. 100°–105° C. (sintering).

IR(Nujol)cm$^{-1}$: 3460, 3330, 1675.

NMR(CDCl$_3$)δ: 1.17(3H,t,J=6.6 Hz), 2.28(3H,s), 2.14–2.65 (10H,m), 3.9–4.25(3H,m), 4.95(1H,s), 6.22(2H,broad s, NH$_2$), 6.67–7.98(12H,m), 8.06(1H,s,NH)

Elemental analysis: Calcd. for C$_{35}$H$_{37}$F$_2$N$_5$O$_6$: C, 63.53; H, 5.64; N, 10.58; Found: C, 63.30; H, 5.48; N, 10.59.

EXAMPLE 13

A mixture of m-nitrobenzaldehyde (0.63 g), 2-(4-diphenylmethylpiperidino)ethyl acetoacetate (1.55 g), methyl 3-amioncrotonate (0.48 g) and 2-propanol (10 ml) was refluxed with stirring for 8 hours. The solvent was distilled off and the residue was subjected to chromatography using silica gel (80 g). From the fractions eluted with dichloromethane-methanol (40:1, v/v), there was obtained 2-(4-diphenylmethyl-piperidino)ethyl methyl 1,4-dihydro-2,6-dimethyl-4-(3-nitrophenyl)-3,5-pyridinedicarboxylate as an oil. This product was treated with a small amount of isopropyl ether and hexane to give a yellow powder, which was dried over phosphorus pentoxide. Yield 0.76 g (29.9%). m.p. 82°–85° C. (sintering).

IR(CHCl$_3$)cm$^{-1}$: 3340(NH), 1700, 1690 (C=O).

NMR(CDCl$_3$)δ: 0.9–2.2(7H,m,piperidine), 2.32(6Hs,CH$_3$ at positions 2 and 3), 2.54(2H,t,J=6 Hz,—CH$_2$CH$_2$N<), 2.81(2H,m,piperidine), 3.43(2H,d,J=10.8 Hz,

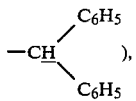

3.59(3H,s,COOCH$_3$), 4.14(2H,t,J=6 Hz,—OCH$_2$CH$_2$—), 5.09 (1H,s,H at position 4), 5.92(1H,s,NH), 7.0–8.1(14H, m,aryl H).

Elemental analysis: Calcd. for C$_{36}$H$_{39}$N$_3$O$_6$: C, 70.92; H, 6.45; N, 6.89; Found: C, 70.56; H, 6.35; N, 6.86.

EXAMPLE 19

A mixture of 2,3-dichlorobenzaldehyde (0.615 g), 2-(4-diphenylmethylpiperidino)ethyl acetoacetate (1.30 g), ethyl 3-aminocrotonate (0.450 g) and 2-propanol (10 ml) was treated in the same manner as Example 13 to give 2-(4-diphenylmethylpiperidino)ethyl ethyl 4-(2,3-dichlorophenyl)-1,4-dihydro-2,6-dimethyl-3,5-pyridinedicarboxylate as a light-yellow powder. Yield 0.272 g (11.9%). m.p. 81°–85° C. (sintering).

IR(CHCl$_3$)cm$^{-1}$: 3350(NH), 1690(C=O)

NMR(CDCl$_3$)δ: 1.14(3H,t,J=7.5 Hz,—CH$_2$CH$_3$), 0.8–2.2(7H,m, piperidine), 2.25(6H,s,CH$_3$ at positions 2 and 6), 2.52(2H,t,J=6 Hz), —CH$_2$CH$_2$N<), 2.77(2H,m,piperdine), 3.45(2H,d,J=10.8 Hz,

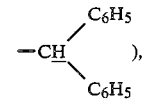

3.9–4.24(4H,m, —OCH$_2$CH$_2$— and —CH$_2$CH$_3$), 5.41(1H,s,H at position 4), 5.73(1H,s,NH), 6.9–7.3(13H,-m,aryl H).

Elemental analysis: Calcd. for C$_{37}$H$_{41}$Cl$_2$N$_2$O$_4$: C, 68.51; H, 6.37; N, 4.32; Found: C, 68.73; H, 6.32; N, 3.93.

EXAMPLE 15

A mixture of 2-(4-phenylpiperidino)ethyl 2-(3-nitrobenzylidene)acetoacetate (500 mg), methyl 2-aminocrotonate (170 mg) and 2-propanol (8 ml) was refluxed for 6 hours. The solvent was distilled off and the residue was subjected to chromatography using silica gel (30 g). From the fractions eluted with chloroform-ethyl acetate-methanol (16:2:1), there was obtained methyl 2-(4-phenylpiperidino)ethyl 1,4-dihydro-2,6-dimethyl-4-(3-nitrophenyl)-3,5-pyridinedicarboxylate as crystals. Recrystallization from 2-propanol gave light-yellow crystals. Yield 87 mg. m.p. 159°–160° C.

IR(Nujol)cm$^{-1}$: 3375(NH), 1710, 1660(C=O).

NMR(CDCl$_3$)δ: 1.6–2.2(7H,m,piperidine), 2.36 and 2.38 (each 3H,s CH at positions 2 and 6), 2.62(2H,t,J=6 Hz, —CH$_2$CH$_2$N<), 2.98(2H,m,piperidine), 3.63(3H,s,—OCH$_3$), 4.20(2H,t,J=6 Hz,—OCH$_2$CH$_2$—), 5.13(1H,s,H at position 4), 5.81(1H,s,NH), 7.1–8.2(9H,m,aryl H).

Elemental analysis: Calcd. for C$_{29}$H$_{33}$N$_3$O$_6$: C, 67.04; H, 6.40; N, 8.09; Found: C, 67.04; H, 6.36; N, 8.09.

REFERENCE EXAMPLE 1

(1) To a mixture of 1-piperazineethanol (11.4 g), potassium carbonate powder (24.3 g) and N,N-dimethylformamide (100 ml) was added dropwise benzhydryl bromide (21.7 g). The mixture was stirred at room temperature for 2 hours, then diluted with water and extracted with ethyl ether. The ethyl ether layer was washed with saturated aquus sodium chloride and dried over sodium sulfate. The solvent was then distilled off and the residue was purified by silica gel chromatography [eluent: hexane-ethyl acetate (2:1)] to give 21.9 g (84.2%) of 4-benzhydryl-1-piperazineethanol as an oil.

IR(Neat): 3380 cm$^{-1}$.

NMR(CDCl$_3$)δ: 2.46(10H,broad s), 3.57(2H,t,J=6.5), 4.20(1H,s), 7.03–7.45(12H,m).

In the same manner as above, the following compounds were obtained:

4-(4,4'-Difluorobenzhydryl)-1-piperazineethanol: Oil
IR(Neat): 3380 cm$^{-1}$.
NMR(CDCl$^3$)δ: 2.2–2.7(10H,m), 3.54(2H,t,J=6), 4.18(1H,s), 6.8–7.4(8H,m).

4-(4,4'-Dichlorobenzhydryl)-1-piperazineethanol: Oil
IR(Neat): 3400 cm$^{-1}$.
NMR(CDCl$_3$)δ: 2.2–2.6(10H,m), 2.82(1H,s,OH), 3.53(2H,t, J=6), 4.14(1H,s), 7.23(8H,s).

4-(4'-Dimethylbenzhydryl)-1-piperazineethanol: Oil

IR(Neat): 3400 cm$^{-1}$.

NMR(CDCl$_3$)δ: 2.24(6H,s), 2.2–2.7(10H,m), 3.54(2H,t,J=6), 4.21(1H,s), 6.9–7.3(8H,m).

(2) Diketene (5.1 g) was added to 4-benzhydryl-1-piperazineethanol (18.1 g) and the mixture was heated at 70°–80° C. with stirring for 1.5 hours and purified by silica gel chromatography [eluent: hexane-ethyl acetate (3:2)] to give 2-(4-benzhydryl-1-piperazinyl)ethyl acetoacetate as an oil. Yield 17.1 g (73.6%).

IR(Neat): 1730, 1715 cm$^{-1}$.

NMR(CDCl$_3$)δ: 2.22(3H,s), 2.43(10H,broad), 3.39(2H,s), 4.18(1H,s), 4.20(2H,t,J=6), 6.64–7.73(10H,m).

In the same manner as above, the following compounds were obtained:

2-[4-(4,4'-Difluorobenzhydryl)-1-piperazinyl]ethyl acetoacetate: Oil

IR(Neat): 1740, 1715 cm$^{-1}$.

NMR(CDCl$_3$)δ: 2.25(3H,s), 2.2–2.7(10H,m), 3.40(2H,s), 4.18(1H,s), 4.25(2H,t,J=6), 6.8–7.5(8H,m).

2-[4-(4,4'-Dichlorobenzhydryl)-1-piperazinyl]ethyl acetoacetate: Oil

IR(Neat): 1740, 1715 cm$^{-1}$.

NMR(CDCl$_3$) δ: 2.23(3H,s), 2.3–2.8(10H,m), 3.42(2H,s), 4.17(1H,s), 4.23(2H,t,J=6), 7.28(8H,s).

2-[4-(4,4'-Dimethylbenzhydryl)-1-piperazinyl]ethyl acetoacetate: Oil

IR(Neat): 1740, 1715 cm$^{31}$ $^1$.

NMR(CDCl$_3$)δ2.23(3H,s), 2.25(6H,s), 2.3–2.8(10H,m), 3.40(2H,s), 4.12(1H,s), 4.23(2H,t,J=6), 7.03(4H,d, J=9), 7.27(4H,d,J=9).

REFERENCE EXAMPLE 2

(1) Ethylene bromohydrin (5.4 g) was added dropwise to a mixture of 1-(3-chlorophenyl)piperazine hydrochloride (5 g), potassium carbonate powder (12 g) and N,N-dimethylformamide (35 ml) with stirring. The mixture was further stirred at room temperature overnight, then diluted with 100 ml of water and extracted with ethyl ether. The ethyl ether layer was washed with saturated aqueous sodium chloride and dried over Na$_2$SO$_4$. The solvent was distilled off and the residue was purified by silica gel chromatography [eluent: ethyl acetate-methanol (4:1)] to give 4.06 g (78.6%) of 4-(3-chlorophenyl)-1-piperazineethanol as an oil.

IR(Neat): 3380 cm$^{-1}$.

NMR(CDCl$_3$)δ: 2.47–2.79(6H,m), 3.06–3.35(5H,m), 3.68(2H, t,J=5.5 Hz), 6.65–7.48(4H,m).

In the same manner as above, the following compound was obtained:

4-(2-Methylphenyl)-1-piperazineethanol: Oil (2) The 4-phenyl-1-piperazineethanols obtained in (1) above were reacted with diketene in the same manner as Reference Example 1-(2) to give the following compounds:

2-[4-(3-Chlorophenyl)-1-piperazinyl]ethyl acetoacetate: Oil

IR(Neat): 1740, 1715 cm$^{-1}$.

NMR(CDCl$_3$)δ: 2.24(3H,s), 2.50–2.82(7H,m), 3.06–3.13(4H, m), 3.44(2H,s), 4.28(2H,t), 6.60–7.36(4H,m).

2-[4-(2-Methylphenyl)-1-piperazinyl ethyl acetoacetate: Oil

REFERENCE EXAMPLE 3

(1) Ethylene bromohydrin (4.03 g) was added dropwise to a mixture of 1-(2,2-diphenylethyl)piperazine (4.30 g), potassium carbonate (6.7 g) and N,N-dimethylformamide (20 ml) with stirring. The mixture was stirred at room temperature overnight, diluted with water and extracted with ethyl acetate. The organic layer was washed with saturated aqueous sodium chloride and dried over Na$_2$SO$_4$. The solvent was then distilled off and the residue was subjected to silica gel chromatography. Elution with ethyl ether-ethyl acetate-methanol (10:2:1, v/v) gave 4-(2,2-diphenylethyl)-1-piperazineethanol as an oil. Yield 4.24 g.

NMR(CDCl$_3$)δ: 2.45(11H,broad s,

—CH$_2$CH$_2$N< and OH), 2.96(2H,d,J=7.5 Hz, >CHCH$_2$N<), 3.55(2H,t,J=5.7 Hz, —OCH$_2$CH$_2$N<), 4.18(1H,t,J=7.5 Hz, >CHCH$_2$—), 7.24(10H, s,aryl H).

(2) Diketene (1.26 g) was added dropwise to 4-(2,2-diphenylethyl)-1-piperazineethanol (4.23 g) obtained in (1) with stirring at 60° C. The mixtue was further stirred with heating at 80° C. and then subjected to silica gel chromatography using ethyl ether-ethyl acetate (5:1, v/v) as the eluent to give 2-[4-(2,2-diphenylethyl)-1-piperazinyl]ethyl acetoacetate as an oil. Yield 4.52 g.

IR(Neat)cm$^{-1}$: 1740, 1710.

NMR(CDCl$_3$)δ: 2.24(3H,s,CH$_3$), 2.44

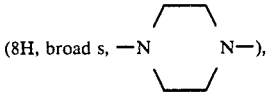

(8H, broad s, —N N—), 2.57(2H,t,J=6 Hz, —CH$_2$CH$_2$N<), 2.95(2H,d,J=7.5 Hz, >NCH$_2$CH<), 3.42(2H,s,—COCH$_2$CO—), 4.17(1H,t,J=7.5 Hz, >NCH$_2$CH<), 4.22(2H,t,J=6 Hz, —CH$_2$CH$_2$N<), 7.20(10H,s, aryl H).

Elemental analysis: Calcd. for C$_{24}$H$_{30}$N$_2$O$_3$: C, 73.07; H, 7.66; N, 7.10; Found: C, 73.08; H, 7.58; N, 7.10.

REFERENCE EXAMPLE 4

(1) Ethylene bromohydrin (0.37 ml) was added dropwise to a mixture of 4-diphenylmethylperidine (1 g), potassium carbonate powder (1.1 g) and N,N-dimethylformamide (10 ml) with stirring, and the mixture was further stirred at room temperature for 4 hours. The precipitate was filtered off and the filtrate was concentrated under reduced pressure, diluted with water and extracted with dichloromethane. The dichloromethane layer was washed with water and dried (MgSO$_4$). The solvent was then distilled off and the residue was purified by silica gel chromatography [eluent: CH$_2$Cl$_2$—MeOH (25:1, v/v)] to give 4-diphenylmethyl-1-piperidineethanol as an oil. Yield 1.08 g (91.9%).

IR(Neat)cm$^{-1}$: 3380.

NMR(CDCl$_3$)δ: 1.0–2.2(7H,m), 2.49(2H,t,J=6 Hz), 2.70–3.0 (2H,m), 3.04(1H,broad s, OH), 3.48(2H,d,J=11.4 Hz), 3.56(2H,t,J=6 Hz), 6.9–7.5(10H,m).

(2) Diketene (0.33 ml) was added to a solution of 4-diphenylmeyl-1-piperidineethanol (1.04 g) in toluene (2 ml) at 70° C. and the mixture was stirred at 70° C. for an hour. The solvent was distilled off under reduced pressure and the residue was purified by silica gel chromatography [hexane-ethyl acetate (2:3, v/v)] to give 2-(4-diphenylmethylpiperidino)ethyl acetoacetate as an oil. Yield 1.23 g (92.1%).

IR(Neat)cm$^{-1}$: 1740, 1720.

NMR(CDCl$_3$)δ: 1.1–2.1(7H,m), 2.23(3H,s), 2.58(2H,t,J=6 Hz), 2.85(2H,m), 3.48(2H,d,J=10.8 Hz), 3.40(2H,s), 4.22(2H,t,J=6 Hz), 6.9–7.3(10H,m).

REFERENCE EXAMPLE 5

(1) Ethylene bromohydrin (0.37 ml) was added dropwise with stirring to a mixture of 4-diphenylmethylpiperidine (1 g), potassium carbonate powder (1.1 g) and N,N-dimethylformamide (10 ml), and the mixture was stirred at room temperature for 4 hours. The precipitate was filtered off and the filtrate was concentrated under reduced pressure, followed by addition of water and extraction with dichloromethane. The dichloromethane layer was washed with water and dried (MgSO$_4$) and the solvent was distilled off. The residue was purified by silica gel chromatography [eluent: CH$_2$Cl$_2$—MeOH (25:1, v/v)] to give 4-diphenylmethyl-1-piperidineethanol as an oil. Yield 1.08 g (91.9%).

IR(Neat)cm$^{-1}$: 3380.

NMR(CDCl$_3$)δ: 1.0–2.2(7H,m), 2.49(2H,t,J=6 Hz), 2.70–3.0(2H,m), 3.04(1H,broad s,OH), 3.48(2H,d,J=11.4 Hz), 3.56(2H,t,J=6 Hz), 6.9–7.5(10H,m).

(2) Diketene (0.33 ml) was added to a solution of 4-diphenylmethyl-1-piperidineethanol (1.04 g) in toluene (2 ml) at 70° C. and the mixture was stirred at 70° C. for an hour. The solvent was distilled off under reduced pressure and the residue was purified by silica gel chromatography [hexane-ethyl acetate (2:3, v/v)] to give 2-(4-diphenylmethylpiperidino)ethyl acetoacetate as an oil. Yield 1.23 g (92.1%).

IR(Neat)cm$^{-1}$: 1740, 1720.

NMR(CDCl$_3$)δ: 1.1–2.1(7H,m), 2.23(3H,s), 2.58(2H,t,J=6 Hz), 2.85(2H,m), 3.48(2H,d,J=10.8 Hz), 3.40(2H,s), 4.22(2H,t,J=6 Hz), 6.9–7.3(10H,m).

REFERENCE EXAMPLE 6

(1) 4-Phenylpiperidine was reacted with ethylene bromohydrin in the same manner as Reference Example 5, and the resulting oily 4-phenyl-1-piperidineethanol was further reacted with diketene to give 2-(4-phenylpiperidino)ethyl acetoacetate as an oil.

IR(Neat)cm$^{-1}$: 1745, 1720.

NMR(CDCl$_3$)δ: 1.7–2.1 7H,m), 2.28(3H,s), 2.67(2H,t,J=6 Hz), 3.01(2H,m), 3.46(2H,s), 4.30(2H,t,J=6 Hz), 7.22(5H,s).

(2) A mixture of m-nitrobenzaldehyde (0.66 g), 2-(4-phenylpiperidino)ethyl acetoacetate (1.2 g), piperidine (0.1 ml) and benzene (20 ml) was refluxed overnight, during which time the water produced was removed azeotropically. The solvent was then distilled off and the residue was chromatographed on silica gel (50 g) [ethyl acetate-hexane (1:1, v/v)] to give 2-(4-phenylpiperidino)-ethyl 2-(3-nitrobenzylidene)acetoacetate as an oil. Yield 0.80 g (45.7%).

IR(Neat)cm$^{-1}$: 1730, 1700, 1670.

What is claimed is:

1. A compound of the formula

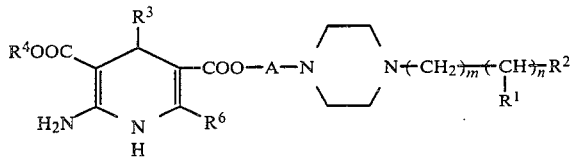

wherein
R$^1$ is hydrogen or phenyl optionally substituted by one or two halo, nitro, trifluoromethyl, C$_{1-6}$-alkyl or C$_{1-3}$-alkoxy groups,
R$^2$ and R$^3$ are phenyl optionally aubstituted by one or two halo, nitro, trifluoromethyl, C$_{1-6}$-alkyl or C$_{1-3}$-alkoxy groups,
R$^4$ and R$^6$ are C$_{1-6}$-alkyl,
A is C$_{2-4}$-alkylene,
m and n are 0 or 1,
or a pharmaceutically acceptable salt thereof.

2. A compound claimed in claim 1, wherein R$^1$, R$^2$ and R$^3$ are the same or different and each is a phenyl.

3. A compound claimed in claim 1, wherein R$^3$ is a phenyl which may be optionally be substituted.

4. A compound claimed claimed claim 1, wherein A is ethylene.

5. A compound claimed in claim 1, which is 5-[2-(4-benzhydryl-1-piperazinyl)ethyl] 3-ethyl 2-amino-1,4-dihydro-6-methyl-4-(3-nitrophenyl)-3,5-pyridinedicarboxylate.

6. A compound claimed in claim 1 which is 5-[2-[4-(4,4'-dimethylbenzhydryl)-1-piperazinyl]-ethyl] 3-ethyl 2-amino-1,4-dihydro-6-methyl-4-(3-nitrophenyl)-3,5-pyridinedicarboxylate.

7. A compound claimed in claim 1, which is 5-[2-[4-(4,4'-difluorobenzhydryl)-1-piperazinyl]ethyl]3-isopropyl 2-amino-1,4-dihydro-6-methyl-4-(3-nitrophenyl)-3,5-pyridinedicarboxylate.

8. A compound claimed in claim 1, which is 5-[2-[4-(4,4'-dichlorobenzhydryl)-1-piperazinyl]ethyl]3-ethyl 2-amino-4-(2,3-dichlorophenyl)-1,4-dihydro-6-methyl-3,5-pyridinedicarboxylate.

9. A compound claimed in claim 1, which is 3-ethyl 5-[2-[4-(4,4'-difluorobenzhydryl)-1-piperazinyl]-ethyl]2-amino-1,4-dihydro-6-methyl-4-(3-nitrophenyl)-3,5-pyridinedicarboxylate.

10. Coronary dilator composition which comprises an effective coronary dilator amount of a compound as defined in claim 1 and a pharmaceutically acceptable carrier or diluent therefor.

11. An anti-hypertensive pharmaceutically composition which comprises an effect anti-hypertensive amount of a compound of the formula

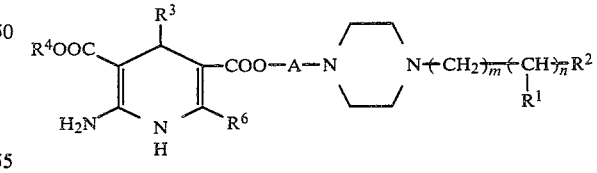

wherein
R$^1$ is hydrogen or phenyl optionally substituted by one or two halo, nitro, trifluromethyl, C$_{1-6}$-alkyl or C$_{1-3}$-alkoxy groups,
R$^2$ and R$^3$ are phenyl optionally substituted by one or two halo, nito, trifluoromethyl, C$_{1-6}$-alkyl or C$_{1-3}$-alkoxy grouns,
R$^4$ and R$^6$ are C$_{1-6}$-alkyl,
A is C$_{2-4}$-alkylene,
m and m are 0 or 1,
or a pharmaceutically acceptable salt thereof, and
a pharmaceutically acceptable carrier or diluent therefor.

* * * * *